US00PP27565P3

(12) United States Plant Patent
Wagner, Sr.

(10) Patent No.: US PP27,565 P3
(45) Date of Patent: Jan. 17, 2017

(54) ***EREMOCHLOA OPHIUROIDES* (MUNRO) HACK PLANT NAMED 'SS-0607'**

(50) Latin Name: ***Eremochloa ophiuroides* (Munro) Hack**
Varietal Denomination: SS-0607

(71) Applicant: Tobey Andrew Wagner, Sr., Mount Pleasant, SC (US)

(72) Inventor: Tobey Andrew Wagner, Sr., Mount Pleasant, SC (US)

( * ) Notice: Subject to any disclaimer, the term of this patent is extended or adjusted under 35 U.S.C. 154(b) by 0 days.

(21) Appl. No.: 14/756,140

(22) Filed: Aug. 6, 2015

(65) Prior Publication Data

US 2016/0050836 P1 Feb. 18, 2016

Related U.S. Application Data

(60) Provisional application No. 61/999,787, filed on Aug. 6, 2014.

(51) Int. Cl.
*A01H 5/12* (2006.01)

(52) U.S. Cl.
USPC ..... Plt./388

(58) Field of Classification Search
USPC ..... Plt./388
See application file for complete search history.

*Primary Examiner* — Annette Para

(57) ABSTRACT

A new and distinct variety of Centipedegrass named 'SS-0607', is characterized by its green and purple stolons, white and purple flowers, long leaf blades, aggressive root system fast lateral growth, compared to other Centipedegrass varieties.

5 Drawing Sheets

Latin name of the genus and species: The Latin name of the genus and species of the novel variety disclosed herein is *Eremochloa ophiuroides* (Munro) Hack and therefore characterizes a new and distinct perennial variety of Centipedegrass.

Variety denomination: The inventive variety of *Eremochloa ophiuroides* (Munro) Hack disclosed herein has been given the variety denomination 'SS-0607'.

BACKGROUND OF THE INVENTION

The present invention relates to a new and distinct perennial variety of *Eremochloa ophiuroides* (Munro) Hack.

'SS-0607' is the selection of *Eremochloa ophiuroides* selected at a sod production field Southwest of Macon, Ga. in 2006. It is unclear the exact pedigree as it was selected in the proximity of two common Centipedegrass production fields. 'SS-0607' was selected due to a distinct fast lateral growth, excellent blocking ability and strong and deep root system. 'SS-0607' has been evaluated in Florida, Texas, North Carolina, Georgia and Mississippi in test plot areas in 2008 and 2009. Primary characteristics of the 'SS-0607' are long leaf blade length, long inflorescence and a pale color seed head. 'SS-0607' has demonstrated excellent fall color retention, good cold hardiness, purple and green stolons. The rate of growth is excellent with average aggressiveness which is beneficial to a low maintenance grass. 'SS-0607' is so identified in pictures and morphological and agronomic charts of this disclosure. It is anticipated that the plant of this invention will be marketed under the synonym 'Santee' as a trade name.

SUMMARY OF THE INVENTION

'SS-0607' is a distinctive variety of *Eremochloa ophiuroides* (Munro) Hack, having a dark green color (10 GY 5/10 on a Munsell Color Chart), long leaf length, long inflorescences, average lateral growth rates and good cold tolerance. 'SS-0607' is propagated primarily by sprigs, rhizomes, plantlets or turf sod, but it can be propagated by seed also. 'SS-0607' is estimated to be adapted for US in zones 7-11 of the USDA Plant Hardiness Zone Map.

BRIEF DESCRIPTION OF THE FIGURES

FIG. 1: 'SS-0607' stolon detail.
FIG. 2: 'SS-0607' leaves with a tint of reddish/light purple color at the tip.
FIG. 3: Green and purple stolons of 'SS-0607'.
FIG. 4: Root structure of 'SS-0707' plugs (left and right).
FIG. 5: 'SS-0607' seed-heads.
FIG. 6: 'SS-0607' and 'SS-0705' plug tray production.
FIG. 7: 'SS-0607' plug detail.
FIG. 8: Test plots with 'SS-0607' near Baton Rouge, La.
FIG. 9: Test plot area being planted with plug trays during 2009.
FIG. 10: Test plot are after planted with plug trays, in 2009.

DESCRIPTION OF THE NEW VARIETY

The following is a detailed description of the new grass variety, based upon observations of the plant grown in field plots at a research area located near Starkville, Miss. 'SS-0607' is an exceptional Centipede grass cultivar with a dark green color (10 GY 5/10 on a Munsell Color Chart). 'SS-0607' is an attractive Centipede grass exhibiting a very fast lateral growth rate and medium internode density. Leaf blades sometimes exhibit a tint of reddish/light purple color at the tip and edges (FIG. 2). 'SS-0607' has green and purple stems and runners (FIG. 1) making it a unique grass. 'SS-0607' performs better in warmer climates and although it has good cold tolerance is best suited for Plant Heat Zones 8-11. 'SS-0607' is a lower maintenance grass due to its reduced aggressiveness and its relative lower Nitrogen fertilization requirements, compared to other warm season grasses like Zoysias and Bermudas. 'SS-0607' is adapted to soils with low pH (<6.0) and to moderate shade. 'SS-0607' has an excellent blocking ability when harvested at a sod farm, due to its strong root and stolons which combined produce a perfect net forming a stable piece of sod.

Dimensions of Morphological Structures

'SS-0607' was compared to an experimental Centipedegrass in a study planted near Starkville, Miss. in 2008. Each variety was planted in 1 gallon pots, using potting mix: Redi-earth Plug and Seedling Mix (Sungro Horticulture, Bellevue, Wash.) and were kept at a green-house to produce plant material for morphological evaluations. Plant material was collected using a completely random experiment design with 4 replications (pots). Greenhouse complex had natural sunlight conditions. The pots were allowed to grow for 4 weeks, and then were clipped once to encourage density and stolon development. They were allowed to grow un-mowed for another 4 weeks before measurement. The leaf blade measurements were conducted from Apr. 1 to Apr. 30, 2008. One hundred and forty randomly selected leaf blades from each cultivar were measured for length and width. Width was measured at the widest point of the blade. The internode measurements were conducted in the same period. All the stolons that grew off each pot were used to measure the internode diameter and internode length. The inflorescence measurements were conducted from September 2009 to November 2009. Thirty seed-heads were randomly selected from each cultivar. The Analysis of Variance (ANOVA) indicated that cultivars differed significantly for most variables measured (Table 1).

TABLE 1

Analysis of Variance for Centipedegrass cultivars comparisons conducted during the 2008 and 2009 growing seasons.

| | Mean Squares of the traits | | | | | | | |
|---|---|---|---|---|---|---|---|---|
| Source | ID (mm) | IL (mm) | LW (mm) | LL (mm) | TIL (mm) | RL (mm) | PL (mm) | NSR |
| Variety | 7.0** | 664.5** | 31.1* | 42334.4** | 249.5** | 162.3** | 71.7** | 260.1** |
| Error | 0.1 | 33.7 | 4.6 | 558.1 | 13.9 | 2.9 | 10.7 | 4.7 |
| CV | 12.0 | 39.5 | 42.0 | 33.7 | 13.8 | 14.1 | 21.8 | 15.1 |

ID—Internode Diameter,
IL—Internode Length,
LL—Leaf Width (mm),
LW—Leaf Length (mm),
TIL—Total Inflorescence Length (mm),
RL—Raceme Length (mm),
PL—Peduncle Length (mm),
NSR—Number of Spikelets per Raceme.
*Significant at 5% level
**Significant at 1% level

TABLE 2

Morphological measurements from unmown greenhouse pots - April, 2008.

| Cultivar | Internode diameter (mm) | Internode length (mm) | Leaf blade width (mm) | Leaf blade length (mm) |
|---|---|---|---|---|
| 'SS-0607' | 2.3 | 16.3 | 5.5 | 82.4 |
| 'SS-0705' | 1.9 | 13.1 | 4.8 | 57.7 |
| LSD(0.05) | 0.1 | 1.4 | 0.5 | 5.6 |
| Number of observations | 140 | 140 | 140 | 140 |

TABLE 3

Inflorescence measurements from unmown greenhouse pots - November, 2009.

| Cultivar | Total inflorescence length[a]—cm | Raceme length[b]—cm | Peduncle length[c]—cm | Number of spikelets per raceme[d] |
|---|---|---|---|---|
| 'Common Centipede' | 9.41 | 4.18 | 5.23 | 15.5 |
| 'SS-0607' | 9.14 | 4.10 | 5.05 | 15.8 |
| 'TifBlair' | 8.26 | 3.70 | 4.56 | 13.9 |
| 'SS0705' | 7.40 | 3.25 | 4.15 | 12.1 |
| LSD (0.05) | 0.60 | 0.27 | 0.53 | 0.11 |

[a]Total inflorescence length is the mean of 30 observations per cultivar including the raceme and peduncle measured from the first node.
[b]Raceme length is the mean of 30 observations per cultivar.
[c]Peduncle length is the mean of 30 observations per cultivar measured from the base of the raceme to the first node.
[d]Number of spikelets per raceme is the mean of 30 observations per cultivar determined by count.

Cultivars showed significant differences on the majority of the analyzed morphological characteristics (Table 1). Internode Diameter (ID), Internode Length (IL), Leaf Length (LL), Total Inflorescence Length (TIL), Raceme Length (RL), Peduncle Length (PL) and Number of Spikelets per Raceme (NSR) were significantly different at 1% level (Table 1). The evaluations were well conducted and produced reliable results as demonstrated by the low Coefficients of Variation (CV) (Table 1).

'SS-0607' has a larger internode diameter (2.30 mm) and a longer internode length (16.3 mm) when compared to 'SS-0705' (1.9 mm and 13.1 mm, respectively) (Table 2). 'SS-0607' also had a longer leaf blade length (82.40 mm) compared to 'SS0507' (57.7 mm) (Table 2). The internode diameter, length and leaf blade length difference between the two varieties were significantly different at 5% level (Table 2). A second distinguish characteristic of 'ss-0607' is that is exhibits green and purple stolons, distributed stand (FIG. 3). A mix of green and purple stolons can be seeing during the growing stages or in the mature stand.

'SS-0607' has long inflorescences; its total inflorescence length (9.14 cm) was significantly longer than the total inflorescence length of 'TifBlair' (8.26 cm) and 'SS-0607' (7.40 cm) (Table 3). 'SS-0607' Total inflorescence length was only shorter than 'Common Centipede' (9.41 cm) (Table 3), but it was not significantly different, since the LSD (0.05)

was 0.60 cm and the actual difference was only 0.27 cm. The inflorescence can be white or purple (FIG. 5) and can be easily seen by a person walking the field.

A more detailed examination of the inflorescence structures, shows 'SS-0607' has the second longest raceme length (4.10 cm) and peduncle length (5.05 cm) (Table 3). 'TifBlair's' raceme length (3.70 cm) and peduncle length (4.56 cm); and 'SS-0705's' raceme length (3.25 cm) and peduncle length (4.15 cm) were statistically shorter than 'SS-0607' (Table 3). 'Common Centipede's' raceme length (4.18 cm) and peduncle length (5.23 cm) were longer than 'SS-0607' (Table 3); however those values were not statistically different to 'SS-0607's' raceme and peduncle's values. In addition to having the second longest total inflorescence length among the compared varieties, 'SS-0607' also exhibits the larger number of spikelets per raceme (15.8), which was statistically different than all other entries in that test (Table 3).

A second comparison study was established in a research area near Baton Rouge, La. in March of 2009 (FIG. 8). Test plots were planted on the ground using plugs produced in 128 cell plug tray, using sprigs of the following varieties and experimental lines: 'common centipede', 'TifBlair', 'SS-0607' and 'SS-0705'. Trays were filled with Redi-earth Plug and Seedling Mix (Sungro Horticulture, Bellevue, Wash.) and a sprig with 3 internodes was planted on each cell (FIG. 7). Trays were irrigated and kept on direct sunlight until cells developed a matured and rooted plug (FIG. 6). After mature, plugs of each variety were planted on 5×7 ft. plots with 3 reps and using 12 inches centers. Plots were irrigated, fertilized, mowed and kept free of weeds and insects. After 100% grown in, plots were used to collect morphological data of each variety.

TABLE 4

Analysis of Variance for Centipedegrass cultivars comparisons conducted during the 2009 growing season.

| | Mean Squares of the traits | | | |
|---|---|---|---|---|
| Source | ID (mm) | IL (mm) | LW (mm) | LL (mm) |
| Variety | 2.26** | 502.0** | 0.84 | 1101.4** |
| Error | 0.1 | 22.3 | 0.62 | 250.1 |
| CV | 13.8 | 36.7 | 17.4 | 29.3 |

ID—Internode Diameter,
IL—Internode Length,
LL—Leaf Width (mm),
LW—Leaf Length (mm)
Significant at 5% level
**Significant at 1% level Cultivars showed significant differences on the following morphological characteristics: Internode Diameter (ID), Internode Length (IL) and Leaf Length (LL). The above mentioned means were significantly different at 1% level (Table 4). The evaluations were well conducted and produced reliable results as demonstrated by the low Coefficients of Variation (CV) (Table 4).

A distinctive characteristic of 'SS-0607' is its long leaf blade and internode length. Table 5 shows 'SS-0607' with the longest internode length (14.5 mm) among the tested varieties. The internode lengths of 'Common centipede' (14.3mm), 'TifBlair' (11.9 mm) and 'SS-0705' (10.8 mm) were statistically different at 5% level (Table 5). 'SS-0607' also exhibits the longest leaf blade length (58.1 mm) compared to 'Common Centipede' (56.3 mm), 'TifBlair' (53.4 mm) and 'SS-0705' (48.2 mm) (Table 5); being statistically different than 'Common Centipede', 'TifBlair' and 'SS-0705' at 5% level (Table 5).

Large internode diameter and long internode length (Tables 2 and 5), allow 'SS-0607' to exhibit a more open canopy and adequate density. Combined with a strong and deep root system (FIG. 4), those characteristics produce a perfect piece of sod, making harvesting more uniform and with less waste.

Furthermore, average aggressiveness and less nitrogen requirements enables 'SS-0607' to produce less scalping when maintained with less mowing and lower inputs, making it ideal for a low maintenance lawn.

TABLE 5

Morphological measurements from mowed field plots - November, 2009.

| Cultivar | Internode diameter (mm) | Internode length (mm) | Leaf blade width (mm) | Leaf blade length (mm) |
|---|---|---|---|---|
| 'SS-0607' | 2.1 | 14.5 | 4.4 | 58.1 |
| 'Common centipede' | 2.0 | 14.3 | 4.7 | 56.3 |
| 'TifBlair' | 2.1 | 11.9 | 4.5 | 53.4 |
| 'SS-0705' | 1.9 | 10.8 | 4.5 | 48.2 |
| LSD(0.05) | 0.1 | 1.0 | NS | 5.7 |
| Number of observations | 150 | 150 | 60 | 60 |

A third set of test plots was planted at sod farms in Texas, North Carolina, South Carolina, Alabama and Georgia during 2009; using the same plug trays produced as described previously (FIGS. 9 and 10). Plots had the same dimensions (5×7 ft. with 3 reps) and plugs were planted using the same spacing (12 inch centers).

'SS-0607' proved to be very aggressive and it was the cultivar with the highest % of ground cover by August 10 (94.0%) (Table 6), most like due to its strong root system and a natural ability of its stolons to grow and cover the ground.

TABLE 6

% of Cover of 'SS-0607' and other cultivars at 5 locations in 2009.

| # | Cultivar | June 21 | July 13 | July 25 | August 10 | August 31 |
|---|---|---|---|---|---|---|
| 1 | 'SS-0705' | 31.7 | 76.7 | 81.7 | 90.0 | 100.0 |
| 2 | 'J1' | 41.7 | 83.3 | 90.0 | 89.0 | 99.7 |
| 3 | 'J2' | 30.0 | 71.7 | 76.7 | 81.7 | 96.7 |
| 4 | 'SS-0607' | 38.3 | 81.7 | 85.0 | 94.0 | 100.0 |
| 5 | 'R2' | 50.0 | 85.0 | 90.0 | 92.7 | 100.0 |
| 6 | 'TifBlair' | 36.7 | 81.7 | 81.7 | 89.0 | 100.0 |
| 7 | 'Common centipede' | 43.3 | 83.3 | 85.0 | 92.3 | 100.0 |
| | LSD (0.05) | 8.5 | 6.5 | 8.2 | 6.9 | NS |

That which is claimed is:

1. A new and distinct variety of Centipedegrass named 'SS-0607', as herein illustrated and described, characterized by its distinctive and unique combination of several characteristics such as: green and purple stolons, white and purple flowers, long leaf blade, aggressive root system and fast lateral growth.

* * * * *

Figure 1 – 'SS-0607' stolon detail.
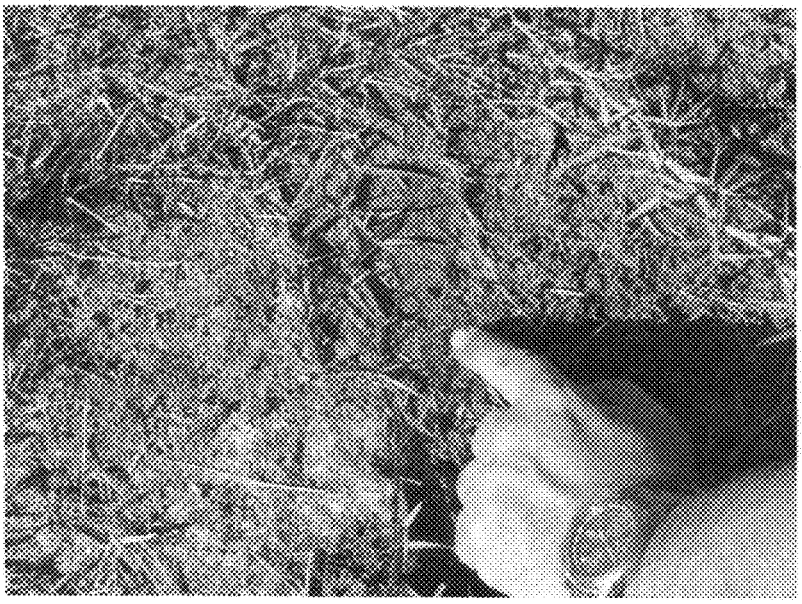
Figure 2 – 'SS-0607' leaves with a tint of reddish/light purple color at the tip.
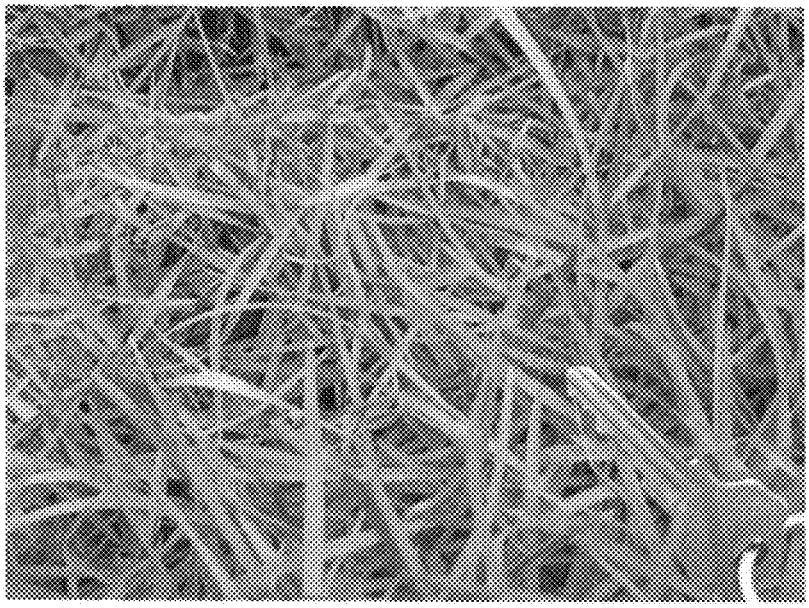

Figure 3 – Green and purple stolons of 'SS-0607'.
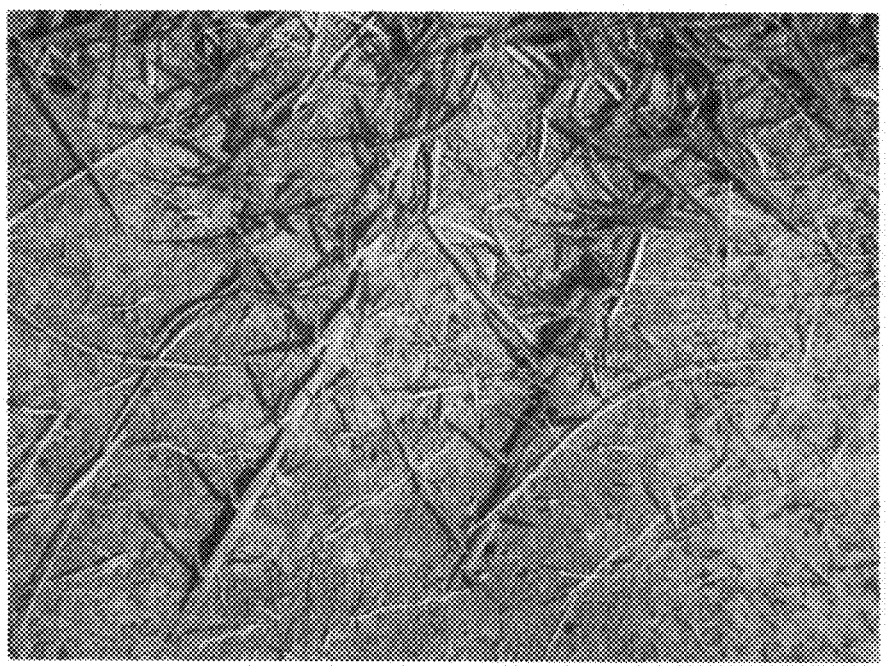
Figure 4 – Root structure of 'SS-0707' plugs (left and right).
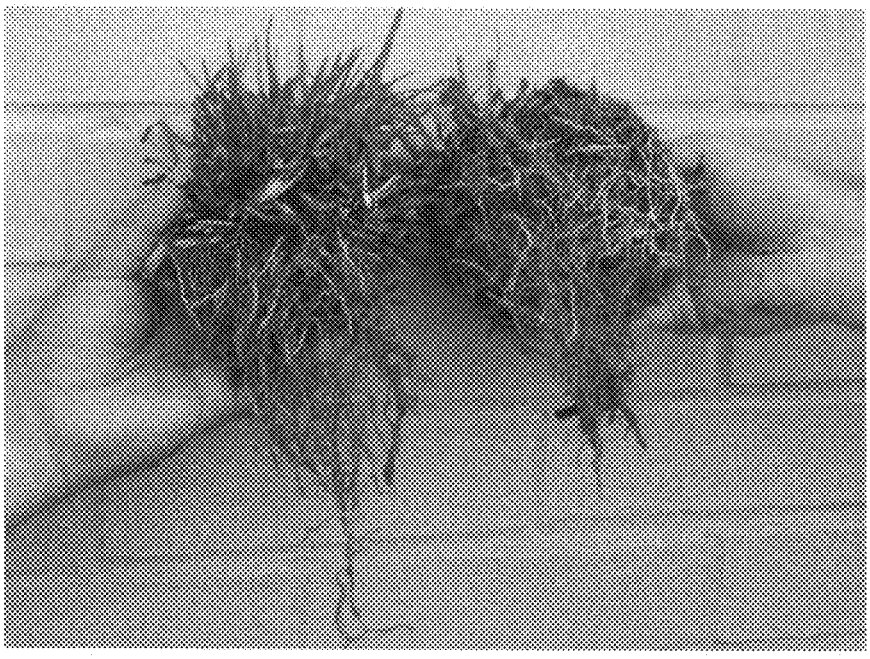

Figure 5 - 'SS-0607' seed-heads.
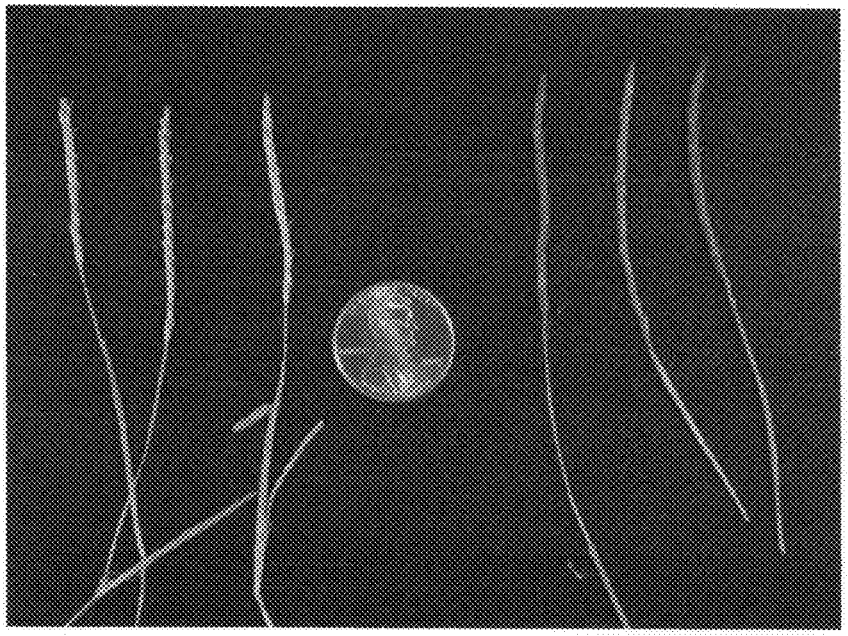
Figure 6 – 'SS-0607' and 'SS-705' plug tray production.
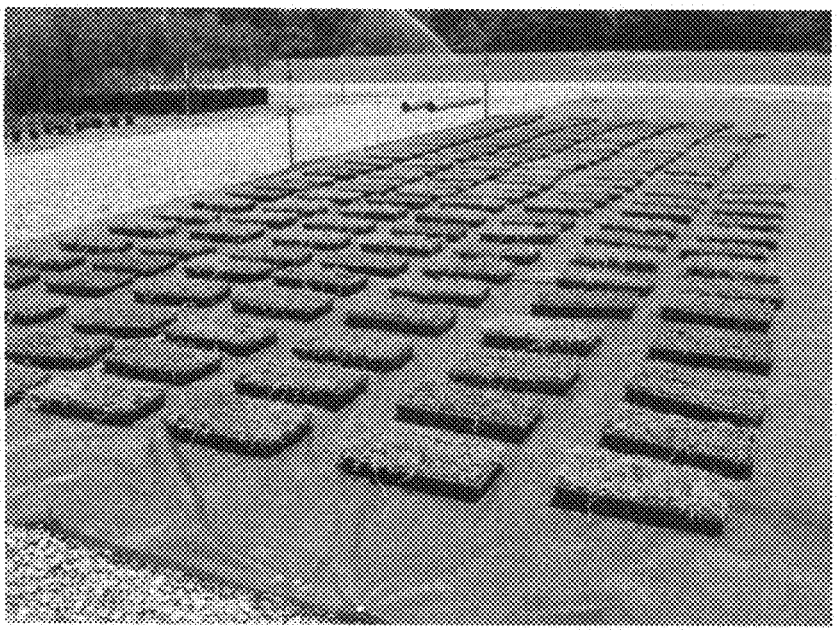

Figure 7 – 'SS-0607' plug detail.
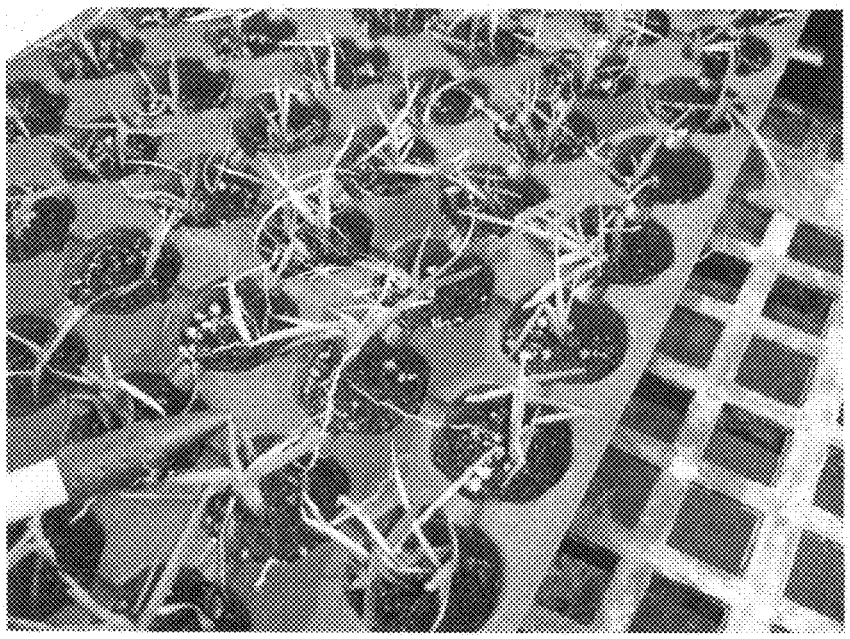
Figure 8 – Test plots with 'SS-0607' near Baton Rouge, LA.
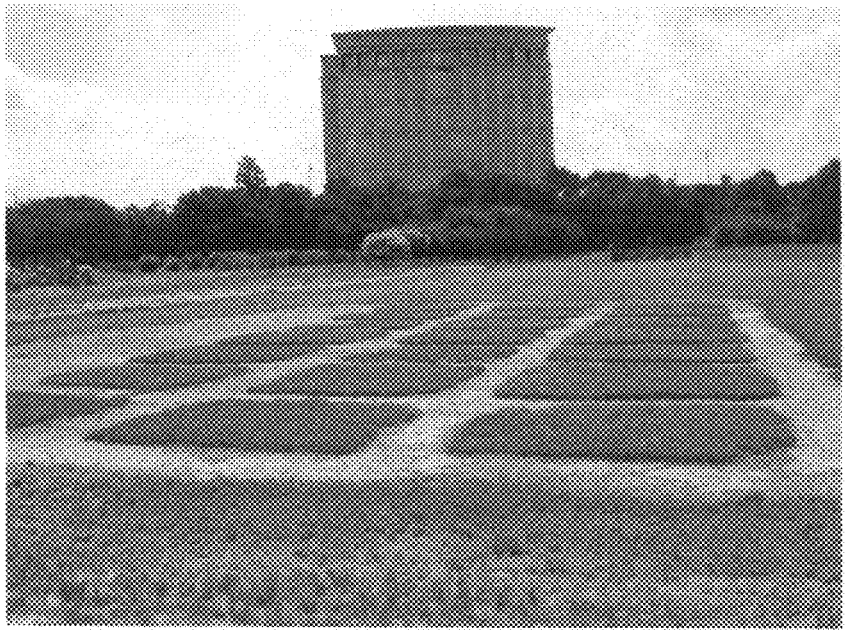

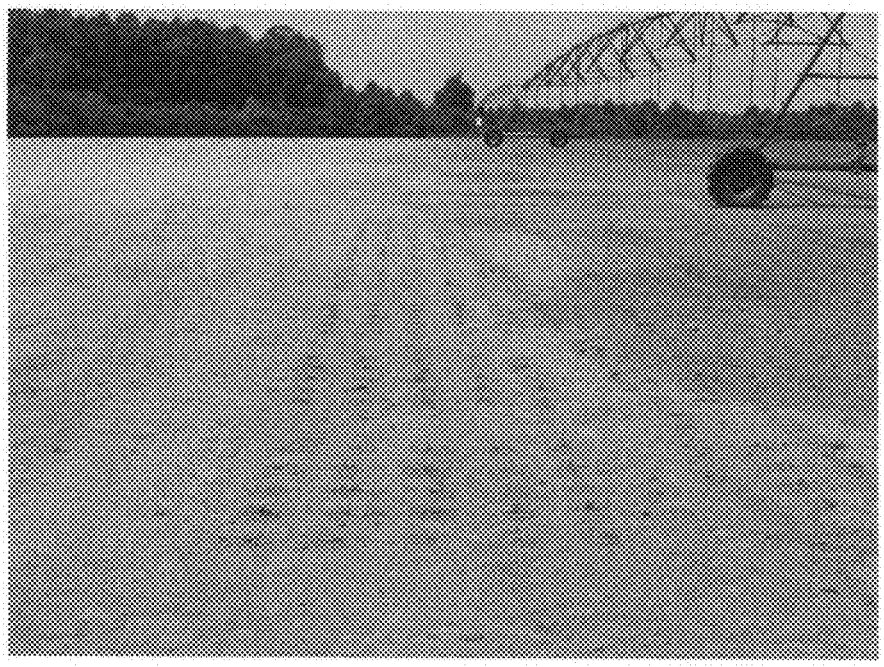

Figure 9. Test plot area being planted with plug trays during 2009.
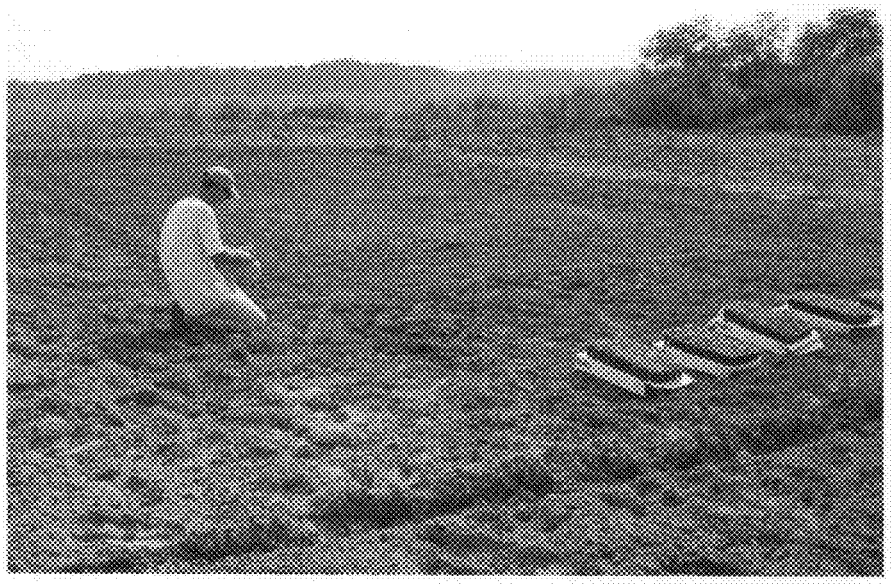
Figure 10. Test plot are after planted with plug trays, in 2009.